US00PP23264P2

(12) United States Plant Patent
Bartels

(10) Patent No.: US PP23,264 P2
(45) Date of Patent: Dec. 18, 2012

(54) ***PHLOX* PLANT NAMED 'BARSEVENTYTWO'**

(50) Latin Name: *Phlox subulata*
Varietal Denomination: Barseventytwo

(75) Inventor: Gosen B. H. Bartels, Aalsmeer (NL)

(73) Assignee: Bartels Breeding B.V., Aalsmeer (NL)

( * ) Notice: Subject to any disclaimer, the term of this patent is extended or adjusted under 35 U.S.C. 154(b) by 0 days.

(21) Appl. No.: 13/136,335

(22) Filed: Jul. 29, 2011

(51) Int. Cl.
*A01H 5/00* (2006.01)

(52) U.S. Cl. ..... Plt./320

(58) Field of Classification Search ..... Plt./320
See application file for complete search history.

*Primary Examiner* — Howard Locker
(74) *Attorney, Agent, or Firm* — Jondle & Associates, P.C.

(57) ABSTRACT

A new *phlox* plant named 'Barseventytwo' particularly distinguished by its lavender flowers and plant vigor, is disclosed.

1 Drawing Sheet

Genus and species: *Phlox subulata.*
Variety denomination: 'Barseventytwo'.

BACKGROUND OF THE NEW PLANT

The present invention comprises a new and distinct variety botanically known as *Phlox subulata*, and hereinafter referred to by the variety name 'Barseventytwo'. The new variety originated from a controlled hybridization in April of 2007 in Aalsmeer, the Netherlands between the female parent, proprietary *phlox* plant 'PS018' (unpatented), and the male parent, proprietary *phlox* plant 'PS003' (unpatented).

'Barseventytwo' was first propagated by cuttings in Aalsmeer, The Netherlands in 2007, and has been subsequently asexually propagated. 'Barseventytwo' has been found to retain its distinctive characteristics through successive asexual propagations via vegetative cuttings for more than 5 generations.

Plant Breeder's Rights application for 'Barseventytwo' was filed in Europe on Jun. 23, 2011 and assigned application number 20111560. 'Barseventytwo' has not been sold or made publicly available more than one year prior to filing of this application.

SUMMARY OF THE INVENTION

The following are the most outstanding and distinguishing characteristics of this new variety when grown under normal horticultural practices in Aalsmeer, The Netherlands.

1. Lavender flowers; and
2. Outstanding plant vigor.

DESCRIPTION OF THE PHOTOGRAPHS

This new *phlox* plant is illustrated by the accompanying photograph which shows the flower blooms, buds, and foliage of the plant. The colors shown are as true as can be reasonably obtained by conventional photographic procedures. The photograph was taken in Aalsmeer, The Netherlands in February of 2011.

DESCRIPTION OF THE NEW VARIETY

The following detailed description sets forth the distinctive characteristics of 'Barseventytwo'. The data which defines these characteristics were collected from asexual reproductions carried out in Aalsmeer, The Netherlands. The plant history was taken on 6 month old plants. Color readings were taken under natural light. Color references are primarily to The R.H.S. Colour Chart.

DETAILED BOTANICAL DESCRIPTION

Classification:
- *Family.*—Polemoniaceae.
- *Botanical name.*—*Phlox subulata.*
- *Common name.*—*Phlox.*
- *Denomination.*—'Barseventytwo'.

Parentage:
- *Female parent.*—'PS018'.
- *Male parent.*—'PS003'.

Plant:
- *Plant habit.*—Compact, creeping, outwardly spreading and mounded.
- *Growth habit.*—Vigorous and freely-branching.
- *Form.*—Compact.
- *Height (measured from the top of the soil).*—10.0 cm to 20.0 cm.
- *Diameter or area of spread.*—20.0 cm to 30.0 cm.
- *Diameter or area of spread (2-year old plant).*—Approximately 40.0 cm.
- *Propagation.*—Vegetative cuttings.
- *Time to produce a finished flowering plant.*—25 to 30 weeks.
- *Lastingness of inflorescence on the plant.*—4 weeks.
- *Outdoor plant performance.*—Good.
- *Time to initiate and develop roots.*—3 weeks.
- *Time to produce rooted cutting or liner (young plant).*—5 weeks.
- *Root description.*—Many tiny roots.

Branches:
- *Habit.*—Creeping.
- *Number of branches per plant.*—At least 10, quickly dividing into new branches.
- *Length of lateral branches.*—20.0 cm to 30.0 cm.
- *Diameter of spread of lateral branches.*—15.0 cm.

Stems:
- *Shape in cross-section.*—Round.
- *Color.*—RHS 199D.

*Diameter.*—1.0 mm.
*Pubescence*.—Absent.

Leaves:
*Arrangement*.—Opposite.
*Color*.—Immature leaf (both upper and lower surfaces): RHS 137B. Mature leaf: Upper surface: RHS 139A. Lower surface: RHS 137A.
*Apex*.—Acute.
*Base*.—Truncated.
*Margin*.—Smooth.
*Length.*—15.0 mm.
*Width.*—2.0 mm.
*Shape*.—Acicular.
*Texture*.—Smooth.
*Venation*.—One single vein in the middle of the leaf.
*Petiole*.—None.

Peduncle:
*Color*.—RHS 199D.
*Length.*—25.0 mm.
*Diameter.*—0.5 mm to 0.8 mm.

Inflorescence:
*Inflorescence type*.—Cyme.
*Blooming habit*.—Abundant flowers.
*Height.*—45.0 mm.
*Width.*—45.0 mm.
*Natural flowering season*.—Spring (April to May).
*Flower number per inflorescence.*—3 to 6.

Flowers:
*Flower bud*.—Size: 12.0 mm.
*Individual bloom/floret*.—Diameter: Approximately 9.0 mm.
*Pedicel*.—Color: RHS 137A. Length: 10.0 mm. Diameter: 0.5 mm.
*Sepals*.—Number: 5. Shape: Fused. Length: 8.0 mm. Width: 2.0 mm. Color (both upper and lower surfaces): RHS 137A.
*Corolla*.—Length: 12.0 mm. Width: 3.0 mm. Fragrance: Slight fragrance.
*Petals*.—Length: 15.0 mm. Width: 9.0 mm. Number: 5. Shape: Obcordate, fused at base. Color: Upper surface (base color and at center): RHS 76A. Outside of corolla tube: RHS 76A.

Reproductive organs:
*Stamens*.—Quantity (per flower): 5. Anther color: RHS 12C. Pollen color: RHS 12C.
*Pistil*.—Quantity: 1. Color: RHS 137A. Size: 2.0 mm.
*Style*.—Length: 8.0 mm. Shape: Three lobes.

Disease and insect resistance: Not observed.

COMPARISON WITH COMMERCIAL VARIETY

'Barseventytwo' differs from the commercial variety 'Emerald Cushion Blue' (unpatented) in that 'Barseventytwo' has lavender flowers (RHS 76A), while 'Emerald Cushion Blue' has light pink flowers (RHS 69D).

I claim:

1. A new and distinct variety of *phlox* plant named 'Barseventytwo' as shown and described herein.

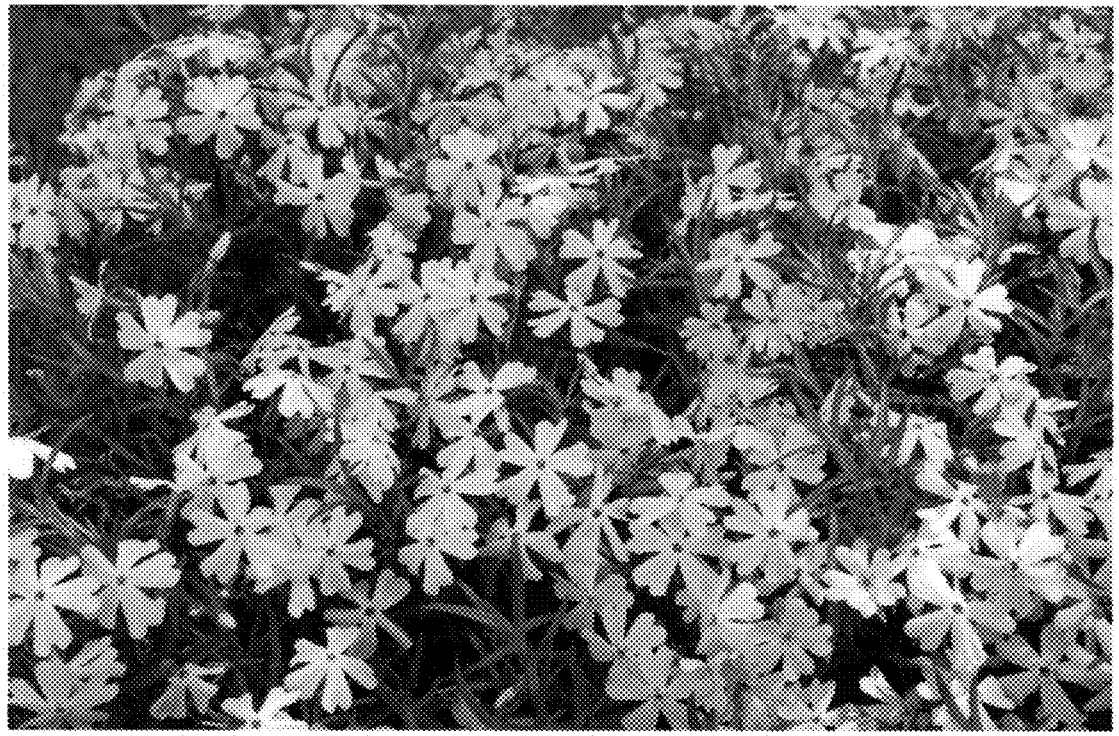

* * * * *